United States Patent [19]

Hayashi et al.

[11] Patent Number: 5,849,529
[45] Date of Patent: Dec. 15, 1998

[54] CELLOBIOSE PHOSPHORYLASE GENE, VECTOR AND TRANSFORMANT CONTAINING SAID GENE

[75] Inventors: Kiyoshi Hayashi, Tsuchiura; Aimin Liu, Tsukuba; Hebiao Li, Tsukuba; Kazutomo Haraguchi, Tsukuba; Yoshiaki Kitamura, Tsukuba, all of Japan

[73] Assignee: Director of National Food Research Institute, Ministry of Agriculture, Forestry and Fisheries, Tsukuba, Japan

[21] Appl. No.: 939,002

[22] Filed: Sep. 26, 1997

[30] Foreign Application Priority Data

Aug. 4, 1997 [JP] Japan .................................. 9-221193

[51] Int. Cl.$^6$ .......................... C12N 15/00; C12N 15/63; C12N 15/85; C12N 1/20
[52] U.S. Cl. ..................... 435/69.1; 435/320.1; 435/325; 435/252.1; 435/193
[58] Field of Search ................................. 435/252.1, 325, 435/25.3, 252.33, 193, 69.1, 320.1, 195; 536/23.1

[56] References Cited

PUBLICATIONS

Sasaki, T., Meth. Enzymol., vol. 160, pp. 468–472, 1988.
Reichenbecher, M. et al., EMBL/Genbank/DDBJ Data Banks, Accession No. U56424, 1996.
"Search Record of Homology on the Data Base", 10 pages 1997.
M.A. Tariq, et al., Carbohydrate Research, vol. 275, pp. 67–72, 1995, "Synthesis and Structural Analysis of Disaccharides of 4–O–β–D–Glucopyranosyl–D–Glucosamine and 4–O–β–Glucopyranosyl–2–Deoxy–D–Glucose".
M.A. Tariq, et al., Biochemical and Biophysical Research Communications, vol. 214, No. 2, pp. 568–575, Sep. 24, 1995, "Synthesis of Three Hetero Disaccharides, 4–O–β–Glucopyranosyl–6–Deoxy–D–Glucose, 4–O–β–D–Glucopyranosyl–D–Mannosamine, and 4–O–β–D–Glucopyranosyl–D–Mannose, and Confirmation of Their Structures by C–13 NMR and MS".
Motomitsu Kitaoka, et al., Biosci, Biotech, Biochem., vol. 56, No. 4, pp. 652–655, 1992, "Phosphorolytic Reaction of Cellvibrio Gilvus Cellobiose Phosphorylase".
Motomitsu Kitaoka, et al., J. Biochem., vol. 112, No. 1, pp. 40–44, 1992, "Synthetic Reaction of Cellvibrio Gilvus Gelloboise Phosphorylase".

*Primary Examiner*—Eric Grimes
*Assistant Examiner*—Peter P. Tung
*Attorney, Agent, or Firm*—Oblon, Spivak, McClelland, Maier & Neustadt, P.C.

[57] ABSTRACT

Disclosed is a cellobiose phosphorylase gene coding for a protein consisting of the amino acid sequence of SEQ ID NO: 16 as set forth in the Sequence Listing, a plasmid vector comprising the cellobiose phosphorylase gene and a transformant transformed with the plasmid vector.

4 Claims, No Drawings

CELLOBIOSE PHOSPHORYLASE GENE, VECTOR AND TRANSFORMANT CONTAINING SAID GENE

FIELD OF THE INVENTION

The present invention relates to a cellobiose phosphorylase gene, a plasmid vector and transformant containing said gene.

Cellobiose phosphorylase (EC2.4.1.20) is an enzyme decomposing cellobiose by phosphorolysis through which glucose-1-phosphate and glucose are obtained from cellobiose and phosphoric acid as the starting materials. This enzyme can also synthesize glucosamine-1-phosphate from kitobiose as the starting material and galactose-1-phosphate from lactose as the starting material.

This enzyme also permits the reverse reaction of said reaction (i.e. the reaction of synthesizing e.g. cellobiose from glucose-1-phosphate and glucose) to proceed. Accordingly, it is an enzyme used in synthesizing various phosphosaccharides and disaccharides.

BACKGROUND OF THE INVENTION

As described above, cellobiose phosphorylase is an enzyme involved in synthesizing various phosphosaccharides, as well as in synthesizing disaccharides by the reverse reaction. In the reverse reaction, saccharides such as 2-amino-2-deoxy-D-glucose, mannose, 2-amino-2-deoxy-D-mannose, 2-deoxy-D-glucose, 6-deoxy-D-glucose, D-xylose etc. besides glucose can be used for synthesis of various hetero-disaccharides. These phosphosaccharides and disaccharides are useful substance expected to be developed in the future as materials for foods, pharmaceutical preparations etc.

However, conventionally used cellobiose phosphorylase is only a crude or purified enzyme extracted from microorganisms of the genera Cellvibrio and Clostridium, and no attempt has been made at stable production of said enzyme to improve its industrial application.

SUMMARY OF THE INVENTION

To further utilize cellobiose phosphorylase, the object of the present invention is to contribute to industrial production of said enzyme by expressing the gene of said enzyme through cloning for elucidating the structure of the gene.

As a result of their eager study for elucidating the structural gene of cellobiose phosphorylase, the present inventors succeeded in cloning a cellobiose phosphorylase gene from microorganisms of the genus Cellvibrio having the ability to produce said enzyme to complete the present invention.

The present invention described in claim 1 is a cellobiose phosphorylase gene coding for a protein consisting of the amino acid sequence of SEQ ID NO: 1 in the Sequence Listing (the amino acid sequence shown in SEQ ID NO: 1 is listed separately in the Sequence Listing as SEQ ID NO:16).

The present invention described in claim 2 is a plasmid vector comprising the cellobiose phosphorylase gene of claim 1.

The present invention described in claim 3 is a transformant transformed with the plasmid vector of claim 2.

DETAILED DESCRIPTION OF THE INVENTION

By the present inventors, cellobiose phosphorylase extracted from microorganisms of the genus Cellvibrio having the ability to produce cellobiose phosphorylase was highly purified, and its N-terminal amino acid sequence was determined. Further, this cellobiose phosphorylase was digested with an enzyme to prepare peptide fragments, and their amino acid sequences were determined.

Then, primers (SEQ ID NOS: 13 and 14) were prepared based on nucleotide sequences deduced from these amino acid sequences. The primers were used in polymerase chain reaction (PCR) using as a template genomic DNA extracted from microorganisms of the genus Cellvibrio, whereby a clear band of a 820 bp DNA nucleotide sequence was obtained.

The resulting band (PCR product) was cloned and sequenced using a DNA sequencer (see SEQ ID NO: 15). When the DNA nucleotide sequence thus determined was translated into amino acids, amino acid sequences corresponding to the previously obtained peptide fragments (see SEQ ID NOS: 3 to 7) were present, so these peptide fragments were found to be parts of a product of the cellobiose phosphorylase gene.

Then, the cellobiose phosphorylase gene was cloned using this PCR product as a probe.

First, genomic DNA extracted from microorganisms of the genus Cellvibrio was disgusted with enzyme and subjected to in vitro packaging into lambda-phase to prepare a phage library.

This phage library was screened for phage carrying the cellobiose phosphorylase gene by use of the above PCR product as a probe, and said gene was extracted from the resulting positive phage.

Further, the gene was extracted from the phage and decomposed with a restriction enzyme and the resulting DNA fragments were subjected to Southern hybridization. As a result, it was confirmed that the target cellobiose phosphorylase gene is present in a 3.1 kbp DNA fragment.

The fragment containing the cellobiose phosphorylase gene was sub-cloned to prepare a plasmid. This plasmid was used to transform E. Coli in a usual manner to give a transformant.

Hereinafter, the present invention is described in detail.

As described above, the cellobiose phosphorylase gene of the present invention is derived from microorganisms of the genus Cellvibrio having the ability to produce cellobiose phosphorylase.

Such Cellvibrio strains having the ability to produce cellobiose phosphorylase include *Cellvibrio gilvus* ATCC 13127 etc.

Cellobiose phosphorylase can be obtained from the above microorganism. Specifically, the above strain is cultured in a nutrient medium in a usual manner, and then the microorganism is separated from the culture and disrupted in a usual manner and centrifuged to give a cellobiose phosphorylase fraction. Then, purification means such as column chromatography, FPLC, HPLC etc. can be used to obtain highly purified cellobiose phosphorylase.

Then, this purified cellobiose phosphorylase was determined for its N-terminal amino acid sequence. For sequencing, protein sequencer Model 477A (manufactured by Perkin Elmer) was used. The determined N-terminal amino acid sequence is as shown in SEQ ID NO: 2 in the Sequence Listing.

Further, this cellobiose phosphorylase was digested with an enzyme to prepare peptide fragments which were then determined for their amino acid sequences (see SEQ ID NO: 3 to 12 in the Sequence Listing).

The nucleotide sequence of the target gene was deduced from the amino acid sequences thus determined. Primers (SEQ ID NOS: 13 and 14) were prepared based on the deduced nucleotide sequence and these were used in PCR where genomic DNA extracted from microorganisms of the genus Cellvibrio was used as a template. As a result, a clear band of a 820 bp DNA nucleotide sequence was obtained.

The resulting band (PCR product) was cloned and then determined for its DNA nucleotide sequence in a DNA sequencer (see SEQ ID NO: 15). When this DNA nucleotide sequence was translated into amino acids, amino acid sequences corresponding to the previously obtained peptide fragments (see SEQ ID NOS: 3 to 7 in the Sequence Listing) were present, so these peptide fragments were found to be parts of a product of the cellobiose phosphorylase gene.

Then, the cellobiose phosphorylase gene was cloned using this PCR product as a probe.

First, DNA was extracted from microorganisms of the genus Cellvibrio and cleaved with a restriction enzyme to give a fraction, which was then subjected to in vitro packaging into lambda-phage to prepare a phage library.

The phage library was screened for phage having the cellobiose phosphorylase gene by use of the above PCR product as a probe to give positive phage.

The gene is extracted from the positive phage and digested with a restriction enzyme to give partial digests which are then, after being separated by agarose gel electrophoresis, subjected to Southern hybridization (page 157 in "Cloning and Sequence" compiled by Watanabe and published by Noson Bunkasha (1989)). As a result, it was confirmed that the target cellobiose phosphorylase gene is present in a 3.1 kbp DNA fragment.

The cellobiose phosphorylase gene of the present invention has the nucleotide sequence of SEQ ID NO: 1 in Sequence Listing.

The cellobiose phosphorylase according to the present invention is an enzyme having a novel amino acid sequence, and no protein with 65% or more homology thereto was found.

Then, this 3.1 kbp DNA fragment was separated by agarose gel electrophoresis and sub-cloned in a previously dephosphorylated plasmid by use of a DNA ligation kit (produced by Takara Shuzo Co., Ltd.) to prepare plasmid pUC-2.

Further, this plasmid was transformed into *E. coli*.

The transformed *E. coli* (*E. coli* pUC-2) has been deposited with the National Institute of Bioscience and Human-Technology, Agency of Industrial Science and Technology, Japan, and its accession number is FERM BP-6033. Plasmid pUC-2 contains the cellobiose phosphorylase gene.

The expression of cellobiose phosphorylase can be confirmed by culturing the resulting *E. coli* transformant and measuring cellobiose phosphorylase in the *E. coli* or the culture supernatant (Journal of Biochemistry, 112, 40–44 (1992)).

This transformant is cultured in a nutrient medium at 20° to 37° C. for 1 to 3 days, and the grown microorganism is disrupted and separated into solid and liquid, and the resulting supernatant is purified in a usual manner to give cellobiose phosphorylase.

EXAMPLES

Hereinafter, the present invention is described in more detail by reference to Examples, which however are not intended to limit the present invention.

Example 1

*Cellvibrio gilvus* ATCC 13127 was cultured in a nutrient medium and the microorganism was then separated from the culture. Then, said microorganism was disrupted in a usual manner and centrifuged to give a disruption liquid, which was then purified by hydrophobic chromatography, ion-exchange chromatography, whereby highly purified cellobiose phosphorylase was obtained.

This purified cellobiose phosphorylase was determined for its N-terminal sequence in Protein Sequencer Model 477A (Perkin Elmer). The sequence thus determined is shown in SEQ ID NO: 2 in the Sequence Listing.

Further, this cellobiose phosphorylase was digested with lysyl endopeptidase (Merck) to give peptide fragments, and 10 peptide fragments were determined for their amino acid sequences. The determined amino acid sequences are shown respectively in SEQ ID NOS: 3 to 12 in the Sequence Listing.

Forward primers and reverse primers were prepared respectively based on 6 selected regions with less codon degeneracy in the determined amino acid sequences. A combination of these primers was used for amplification by PCR where genomic DNA from *Cellvibrio gilvus* ATCC 13127 was used as a template.

The result indicated that a 820 bp clear band was obtained by PCR when the forward primer shown in SEQ ID NO: 13 in the Sequence Listing and the reverse primer shown in SEQ ID NO: 14 in the Sequence Listing were selected as a combination of primers.

The resulting band was cloned, and its analysis in a DNA sequencer revealed the DNA nucleotide sequence of SEQ ID NO: 15. When this DNA nucleotide sequence was translated into amino acids, amino acid sequences corresponding to the amino acid sequences of SEQ ID NOS: 3 to 7 out of the previously obtained peptide fragments were present, so these peptide fragments were found to be parts of a product of the cellobiose phosphorylase gene.

Then, the cellobiose phosphorylase gene was cloned using this PCR product as a probe. Genomic DNA was extracted from *Cellvibrio gilvus* ATCC 13127 by the Saito's method ("Tanpakushitsu Kakusan Kouso" (Protein, Nucleic Acid and Enzyme), vol. 11, page 446). This genomic DNA was partially digested with restriction enzyme Sau III Al and then ultracentrifuged so that an about 20 kbp fraction was obtained. This fraction was subjected to in vitro packaging into lambda-phase by use of Gigapack II Gold (Stratagene) to prepare a phage library.

The phage library was screened for phage carrying the cellobiose phosphorylase gene by using the above probe in a usual manner (page 134 in "Cloning and Sequence" compiled by Watanabe and published by Noson Bunkasha (1989)). As a result, 5 positive phages were obtained.

Further, the gene was extracted from the phage and partially digested with restriction enzymes Sac I and Pst I, and the resulting restriction enzyme digests were separated by agarose gel electrophoresis and subjected to Southern hybridization (page 157 in "Cloning and Sequence" compiled by Watanabe and published by Noson Bunkasha (1989)). As a result, it was confirmed that the target cellobiose phosphorylase gene is present in a 3.1 kbp DNA fragment.

Then, this 3.1 kbp fragment was separated by agarose gel electrophoresis according to the method described by Sambrook, J., Fritsch, E. F. and Maniatis, T. in Molecular Cloning, A Laboratory Manual, 2nd edition, Ch. 6.3, Vol. 1 (1989).

Separately, plasmid pUC-18 was decomposed with restriction enzymes Sac I and Pst I and then dephosphorylated with alkaline phosphatase. The above 3.1 kbp fragment was sub-cloned in this dephosphorylated plasmid by using a DNA ligation kit (Takara Shuzo Co., Ltd.) in a usual manner (see the method described on page 134 in "Cloning and Sequence" compiled by Watanabe and published by Noson Bunkasha (1989)), whereby plasmid pUC-2 was prepared.

Further, this plasmid was transformed into *E. coli* according to the method described by Sambrook, J., Fritsch, E. F. and Maniatis, T. in Molecular Cloning, A Laboratory Manual, 2nd edition, Ch. 1.74, Vol. 1 (1989).

The transformed *E. coli* has been deposited with the National Institute of Bioscience and Human-Technology, Agency of Industrial Science and Technology, Japan, and its accession number is FERM BP-6033. Plasmid pUC-2 contains the cellobiose phosphorylase gene.

Plasmid pUC-2 was prepared in a large amount from the transformant thus obtained and determined for its nucleotide sequence by use of d-rhodamine terminator cycle sequencing kit (Perkin Elmer).

By combining the information of the determined nucleotide sequences, the cellobiose phosphorylase gene was constituted. The nucleotide sequence of said gene and its coding amino acid sequence are as shown in SEQ ID NO: 1.

The amino acid sequence as shown in SEQ ID NO: 1 in the Sequence Listing, encoded by the cellobiose phosphorylase gene, was compared with the previously revealed amino acid sequences.

As a result, the N-terminal amino acid sequence (see SEQ ID NO: 2 in the Sequence Listing) of cellobiose phosphorylase agreed with the partial sequence at the 1- to 42-positions in the amino acid sequence as shown in SEQ ID NO: 1.

Further, the sequences of peptide fragments derived from cellobiose phosphorylase (SEQ ID NOS: 3, 4, 5, 6, 7, 8, 9, 10, 11 and 12) agreed with the partial sequences at the 90- to 114-positions, 115- to 131-positions, 132- to 142-positions, 189- to 219-positions, 235- to 252-positions, 278- to 288-positions, 289- to 319-positions, 411- to 424-positions, 551- to 557-positions and 590- to 618-positions in the amino acid sequence as shown in SEQ ID NO: 1.

When the molecular weight of active cellobiose phosphorylase was determined with laser ionization TOF-MS KOMPACT MALDI III (Shimadzu), its molecular weight was 91,000 Dalton which agreed well with the molecular weight 90,813 of the protein encoded by the present gene.

From the above results, the cellobiose phosphorylase gene was found in the nucleotide sequence. That is, the structural gene of cellobiose phosphorylase was confirmed to be located within the 359- to 2827-positions in the nucleotide sequence.

According to the present invention, there is provided the cellobiose phosphorylase gene. The enzyme obtained by expressing the gene permits phosphorolysis reaction or its reverse reaction to proceed, thus efficiently producing various phosphosaccharides and heterodisaccharides useful in the fields of food manufacturing industry and pharmaceutical industry.

The entire disclosure of Japanese Patent Application No. 9-221193 filed on Aug. 4, 1997 including specification, claims and summary are incorporated herein by reference in its entirety.

What is claimed is:

1. An isolated cellobiose phosphorylase gene encoding a protein consisting of the amino acid sequence of SEQ ID NO: 16.

2. A plasmid vector comprising the cellobiose phosphorylase gene of claim 1.

3. A transformant transformed with the plasmid vector of claim 2.

4. A method of producing cellobiose phosphorylose comprising culturing the transformant of claim 3 in a culture medium, and isolating the cellobiose phosphorylase.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 3157 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cellvibrio gilvus
        ( B ) STRAIN: ATCC 13127
        ( C ) INDIVIDUAL ISOLATE: Direct Origin: pUC-2

( i x ) FEATURE:
        ( A ) NAME/KEY: mat_peptide
        ( B ) LOCATION: 359..2824
        ( D ) OTHER INFORMATION: /note= "METHOD FOR DETERMINING
            SEQUENCE: E"

( i x ) FEATURE:
        ( A ) NAME/KEY: CDS
        ( B ) LOCATION: 359..2824

( x i ) SEQUENCE DESCRIPTION: SEQ ID NO:1:

```
GAGCTCGGCC  CTGATGTCAC  GGTCGGAGAG  CAGCACGGGC  CCACGGTAGT  GCCCCGGACG        60

GGTGTCCGGG  GCCGTCCGCC  CACGCCCGTC  CACGCTCCTC  CCACACCGTT  CCCACACCCC       120
```

```
TGTGCGAGCG TCGCGCAGCC CGCCCGGGGC GCCCGGCCGG AGGGTGCGCA CGGACGTGCG      180

ACCTGCGCCC GTTCTCGTCG GGACCCGCGG CGGCTATGAT CCCTCTCGTG AGGCGCGTGG      240

GAGCGCTCTC GCACCGACCA TGAGCCGCGT CAGAGCCTCG ACGCCGACCC GCACGGACGC      300

GGACGGCCGA CCGGGGGGCC GGGCGCGACA CAACCCGAGC ACCCGAGGGG CACCACCG       358
```

| | | | | | | | | | | | | | | | | |
|---|---|---|---|---|---|---|---|---|---|---|---|---|---|---|---|---|
| ATG | CGG | TAC | GGC | CAT | TTC | GAC | GAC | GCG | GCG | CGC | GAG | TAC | GTC | ATC | ACG | 406 |
| Met | Arg | Tyr | Gly | His | Phe | Asp | Asp | Ala | Ala | Arg | Glu | Tyr | Val | Ile | Thr | |
| 1 | | | | 5 | | | | | 10 | | | | | 15 | | |
| ACG | CCT | CAC | ACC | CCC | TAC | CCG | TGG | ATC | AAC | TAC | CTC | GGG | TCG | GAG | CAG | 454 |
| Thr | Pro | His | Thr | Pro | Tyr | Pro | Trp | Ile | Asn | Tyr | Leu | Gly | Ser | Glu | Gln | |
| | | | 20 | | | | | 25 | | | | | 30 | | | |
| TTC | TTC | TCG | CTG | CTC | TCC | CAC | CAG | GCC | GGC | GGC | TAC | TCG | TTC | TAC | CGC | 502 |
| Phe | Phe | Ser | Leu | Leu | Ser | His | Gln | Ala | Gly | Gly | Tyr | Ser | Phe | Tyr | Arg | |
| | | 35 | | | | | 40 | | | | | 45 | | | | |
| GAC | GCC | AAG | ATG | CGG | CGG | CTC | ACG | CGC | TAC | CGC | TAC | AAC | AAC | ATC | CCC | 550 |
| Asp | Ala | Lys | Met | Arg | Arg | Leu | Thr | Arg | Tyr | Arg | Tyr | Asn | Asn | Ile | Pro | |
| | 50 | | | | | 55 | | | | | 60 | | | | | |
| GCG | GAC | GCG | GGC | GGC | CGG | TAC | CTG | TAC | GTC | AAC | GAC | GGC | GGC | GAC | GTG | 598 |
| Ala | Asp | Ala | Gly | Gly | Arg | Tyr | Leu | Tyr | Val | Asn | Asp | Gly | Gly | Asp | Val | |
| 65 | | | | | 70 | | | | | 75 | | | | | 80 | |
| TGG | ACC | CCG | TCG | TGG | CTG | CCG | GTC | AAG | GCG | GAC | CTG | GAC | CAC | TTC | GAG | 646 |
| Trp | Thr | Pro | Ser | Trp | Leu | Pro | Val | Lys | Ala | Asp | Leu | Asp | His | Phe | Glu | |
| | | | | 85 | | | | | 90 | | | | | 95 | | |
| GCG | CGC | CAC | GGC | CTC | GGC | TAC | TCG | CGC | ATC | ACG | GGC | GAG | CGC | AAC | GGC | 694 |
| Ala | Arg | His | Gly | Leu | Gly | Tyr | Ser | Arg | Ile | Thr | Gly | Glu | Arg | Asn | Gly | |
| | | | 100 | | | | | 105 | | | | | 110 | | | |
| CTG | AAG | GTC | GAG | ACG | CTC | TTC | TTC | GTC | CCG | CTC | GGC | GAG | AAC | GCC | GAG | 742 |
| Leu | Lys | Val | Glu | Thr | Leu | Phe | Phe | Val | Pro | Leu | Gly | Glu | Asn | Ala | Glu | |
| | | 115 | | | | | 120 | | | | | 125 | | | | |
| GTG | CAG | AAG | GTC | ACC | GTC | ACC | AAC | ACG | TCC | GAC | GCC | CCG | AAG | ACG | GCG | 790 |
| Val | Gln | Lys | Val | Thr | Val | Thr | Asn | Thr | Ser | Asp | Ala | Pro | Lys | Thr | Ala | |
| | 130 | | | | | 135 | | | | | 140 | | | | | |
| ACG | CTG | TTC | TCG | TTC | GTC | GAG | TTC | TGC | CTG | TGG | AAC | GCG | CAG | GAC | GAC | 838 |
| Thr | Leu | Phe | Ser | Phe | Val | Glu | Phe | Cys | Leu | Trp | Asn | Ala | Gln | Asp | Asp | |
| 145 | | | | | 150 | | | | | 155 | | | | | 160 | |
| CAG | ACG | AAC | TAC | CAG | CGC | AAC | CTG | TCG | ATC | GGC | GAG | GTC | GAG | GTC | GAG | 886 |
| Gln | Thr | Asn | Tyr | Gln | Arg | Asn | Leu | Ser | Ile | Gly | Glu | Val | Glu | Val | Glu | |
| | | | | 165 | | | | | 170 | | | | | 175 | | |
| CAG | GAC | GGC | CCG | CAC | GGC | TCG | GCG | ATC | TAC | CAC | AAG | ACC | GAG | TAC | CGC | 934 |
| Gln | Asp | Gly | Pro | His | Gly | Ser | Ala | Ile | Tyr | His | Lys | Thr | Glu | Tyr | Arg | |
| | | | 180 | | | | | 185 | | | | | 190 | | | |
| GAG | CGC | CGC | GAC | CAC | TAC | GCC | GTG | TTC | GGC | GTG | AAC | ACC | CGC | GCG | GAC | 982 |
| Glu | Arg | Arg | Asp | His | Tyr | Ala | Val | Phe | Gly | Val | Asn | Thr | Arg | Ala | Asp | |
| | | 195 | | | | | 200 | | | | | 205 | | | | |
| GGC | TTC | GAC | ACG | GAC | CGC | GAC | ACG | TTC | GTG | GGC | GCG | TAC | AAC | TCG | CTG | 1030 |
| Gly | Phe | Asp | Thr | Asp | Arg | Asp | Thr | Phe | Val | Gly | Ala | Tyr | Asn | Ser | Leu | |
| | 210 | | | | | 215 | | | | | 220 | | | | | |
| GGC | GAG | GCG | TCC | GTC | CCG | CGC | GCC | GGG | AAG | TCC | GCG | GAC | TCG | GTC | GCG | 1078 |
| Gly | Glu | Ala | Ser | Val | Pro | Arg | Ala | Gly | Lys | Ser | Ala | Asp | Ser | Val | Ala | |
| 225 | | | | | 230 | | | | | 235 | | | | | 240 | |
| TCG | GGC | TGG | TAC | CCG | ATC | GGC | TCG | CAC | TCC | GTC | GCC | GTG | ACG | CTG | CAG | 1126 |
| Ser | Gly | Trp | Tyr | Pro | Ile | Gly | Ser | His | Ser | Val | Ala | Val | Thr | Leu | Gln | |
| | | | | 245 | | | | | 250 | | | | | 255 | | |
| CCC | GGC | GAG | TCC | CGC | GAC | CTC | GTC | TAC | GTG | CTG | GGC | TAC | CTG | GAG | AAC | 1174 |
| Pro | Gly | Glu | Ser | Arg | Asp | Leu | Val | Tyr | Val | Leu | Gly | Tyr | Leu | Glu | Asn | |
| | | | | 260 | | | | | 265 | | | | | 270 | | |
| CCC | GAC | GAG | GAG | AAG | TGG | GCC | GAC | GAC | GCC | CAC | CAG | GTC | GTC | AAC | AAG | 1222 |
| Pro | Asp | Glu | Glu | Lys | Trp | Ala | Asp | Asp | Ala | His | Gln | Val | Val | Asn | Lys | |
| | 275 | | | | | 280 | | | | | 285 | | | | | |

| | | | | | | | | | | | | | | | | |
|---|---|---|---|---|---|---|---|---|---|---|---|---|---|---|---|---|
| GCG | CCC | GCG | CAC | GCG | CTG | CTG | GGC | CGG | TTC | GCG | ACG | AGC | GAG | CAG | GTC | 1270 |
| Ala | Pro | Ala | His | Ala | Leu | Leu | Gly | Arg | Phe | Ala | Thr | Ser | Glu | Gln | Val | |
| | 290 | | | | 295 | | | | | 300 | | | | | | |
| GAC | GCC | GCC | CTG | GAG | GCG | CTG | AAC | TCC | TAC | TGG | ACG | AAC | CTG | CTC | TCG | 1318 |
| Asp | Ala | Ala | Leu | Glu | Ala | Leu | Asn | Ser | Tyr | Trp | Thr | Asn | Leu | Leu | Ser | |
| 305 | | | | | 310 | | | | | 315 | | | | | 320 | |
| ACG | TAC | TCG | GTG | TCG | AGC | ACC | GAC | GAG | AAG | CTC | GAC | CGG | ATG | GTC | AAC | 1366 |
| Thr | Tyr | Ser | Val | Ser | Ser | Thr | Asp | Glu | Lys | Leu | Asp | Arg | Met | Val | Asn | |
| | | | | 325 | | | | | 330 | | | | | 335 | | |
| ATC | TGG | AAC | CAG | TAC | CAG | TGC | ATG | GTC | ACG | TTC | AAC | ATG | TCG | CGC | TCG | 1414 |
| Ile | Trp | Asn | Gln | Tyr | Gln | Cys | Met | Val | Thr | Phe | Asn | Met | Ser | Arg | Ser | |
| | | | 340 | | | | | 345 | | | | | 350 | | | |
| GCG | TCG | TTC | TTC | GAG | ACG | GGC | ATC | GGC | CGC | GGG | ATG | GGC | TTC | CGC | GAC | 1462 |
| Ala | Ser | Phe | Phe | Glu | Thr | Gly | Ile | Gly | Arg | Gly | Met | Gly | Phe | Arg | Asp | |
| | | 355 | | | | | 360 | | | | | 365 | | | | |
| TCC | AAC | CAG | GAC | CTC | CTG | GGC | TTC | GTG | CAC | CTG | ATC | CCG | GAG | CGC | GCG | 1510 |
| Ser | Asn | Gln | Asp | Leu | Leu | Gly | Phe | Val | His | Leu | Ile | Pro | Glu | Arg | Ala | |
| | 370 | | | | | 375 | | | | | 380 | | | | | |
| CGC | GAG | CGG | ATC | ATC | GAC | ATC | GCC | TCG | ACG | CAG | TTC | GCG | GAC | GGC | TCG | 1558 |
| Arg | Glu | Arg | Ile | Ile | Asp | Ile | Ala | Ser | Thr | Gln | Phe | Ala | Asp | Gly | Ser | |
| 385 | | | | | 390 | | | | | 395 | | | | | 400 | |
| GCG | TAC | CAC | CAG | TAC | CAG | CCG | CTC | ACG | AAG | CGC | GGG | AAC | AAC | GAC | ATC | 1606 |
| Ala | Tyr | His | Gln | Tyr | Gln | Pro | Leu | Thr | Lys | Arg | Gly | Asn | Asn | Asp | Ile | |
| | | | | 405 | | | | | 410 | | | | | 415 | | |
| GGC | TCG | GGC | TTC | AAC | GAC | GAC | CCG | CTG | TGG | CTC | ATC | GCG | GGC | GTG | GCG | 1654 |
| Gly | Ser | Gly | Phe | Asn | Asp | Asp | Pro | Leu | Trp | Leu | Ile | Ala | Gly | Val | Ala | |
| | | | 420 | | | | | 425 | | | | | 430 | | | |
| GCG | TAC | ATC | AAG | GAG | TCC | GGC | GAC | TGG | GGC | ATC | CTC | GAC | GAG | CCC | GTG | 1702 |
| Ala | Tyr | Ile | Lys | Glu | Ser | Gly | Asp | Trp | Gly | Ile | Leu | Asp | Glu | Pro | Val | |
| | | 435 | | | | | 440 | | | | | 445 | | | | |
| CCG | TTC | GAC | AAC | GAG | CCC | GGC | TCC | GAG | GTC | CCG | CTG | TTC | GAG | CAC | CTG | 1750 |
| Pro | Phe | Asp | Asn | Glu | Pro | Gly | Ser | Glu | Val | Pro | Leu | Phe | Glu | His | Leu | |
| | 450 | | | | | 455 | | | | | 460 | | | | | |
| ACG | CGC | TCC | TTC | CAG | TTC | ACG | GTG | CAG | AAC | CGC | GGC | CCG | CAC | GGC | CTG | 1798 |
| Thr | Arg | Ser | Phe | Gln | Phe | Thr | Val | Gln | Asn | Arg | Gly | Pro | His | Gly | Leu | |
| 465 | | | | | 470 | | | | | 475 | | | | | 480 | |
| CCG | CTC | ATC | GGC | CGT | GCC | GAC | TGG | AAC | GAC | TGC | CTC | AAC | CTC | AAC | TGC | 1846 |
| Pro | Leu | Ile | Gly | Arg | Ala | Asp | Trp | Asn | Asp | Cys | Leu | Asn | Leu | Asn | Cys | |
| | | | | 485 | | | | | 490 | | | | | 495 | | |
| TTC | TCG | ACG | ACC | CCG | GGC | GAG | TCG | TTC | CAG | ACG | ACC | GAG | AAC | CAG | GCG | 1894 |
| Phe | Ser | Thr | Thr | Pro | Gly | Glu | Ser | Phe | Gln | Thr | Thr | Glu | Asn | Gln | Ala | |
| | | | | 500 | | | | | 505 | | | | | 510 | | |
| GGC | GGC | GTC | GCG | GAG | TCC | GTG | TTC | ATC | GCG | GCG | CAG | TTC | GTG | CTC | TAC | 1942 |
| Gly | Gly | Val | Ala | Glu | Ser | Val | Phe | Ile | Ala | Ala | Gln | Phe | Val | Leu | Tyr | |
| | | | 515 | | | | | 520 | | | | | 525 | | | |
| GGC | GCG | GAG | TAC | GCC | ACG | CTC | GCG | GAG | CGT | CGC | GGC | CTC | GCG | GAC | GTC | 1990 |
| Gly | Ala | Glu | Tyr | Ala | Thr | Leu | Ala | Glu | Arg | Arg | Gly | Leu | Ala | Asp | Val | |
| | | 530 | | | | | 535 | | | | | 540 | | | | |
| GCC | ACC | GAG | GCG | CGC | AAG | TAC | GTC | GAC | GAG | GTG | CGT | GCC | GCG | GTG | CTC | 2038 |
| Ala | Thr | Glu | Ala | Arg | Lys | Tyr | Val | Asp | Glu | Val | Arg | Ala | Ala | Val | Leu | |
| 545 | | | | | 550 | | | | | 555 | | | | | 560 | |
| GAG | CAC | GGC | TGG | GAC | GGC | CAG | TGG | TTC | CTG | CGT | GCC | TAC | GAC | TAC | TAC | 2086 |
| Glu | His | Gly | Trp | Asp | Gly | Gln | Trp | Phe | Leu | Arg | Ala | Tyr | Asp | Tyr | Tyr | |
| | | | | 565 | | | | | 570 | | | | | 575 | | |
| GGC | AAC | CCG | GTC | GGC | ACG | GAC | GCC | AAG | CCC | GAG | GGC | AAG | ATC | TGG | ATC | 2134 |
| Gly | Asn | Pro | Val | Gly | Thr | Asp | Ala | Lys | Pro | Glu | Gly | Lys | Ile | Trp | Ile | |
| | | | 580 | | | | | 585 | | | | | 590 | | | |
| GAG | CCG | CAG | GGC | TTC | GCC | GTC | ATG | GCG | GGC | ATC | GGC | GTC | GGC | GAG | GGC | 2182 |
| Glu | Pro | Gln | Gly | Phe | Ala | Val | Met | Ala | Gly | Ile | Gly | Val | Gly | Glu | Gly | |
| | | 595 | | | | | 600 | | | | | 605 | | | | |

| | | | | | | | | | | | | | | | | |
|---|---|---|---|---|---|---|---|---|---|---|---|---|---|---|---|---|
| CCG | GAC | GAC | GCG | GAC | GCG | CCG | GCC | GTC | AAG | GCG | CTC | GAC | TCC | GTG | AAC | 2230 |
| Pro | Asp | Asp | Ala | Asp | Ala | Pro | Ala | Val | Lys | Ala | Leu | Asp | Ser | Val | Asn | |
| | 610 | | | | 615 | | | | | 620 | | | | | | |
| GAG | ATG | CTC | GGC | ACG | CCG | CAC | GGC | CTG | GTG | CTG | CAG | TAC | CCG | GCG | TAC | 2278 |
| Glu | Met | Leu | Gly | Thr | Pro | His | Gly | Leu | Val | Leu | Gln | Tyr | Pro | Ala | Tyr | |
| 625 | | | | | 630 | | | | | 635 | | | | | 640 | |
| ACG | ACG | TAC | CAG | ATC | GAG | CTC | GGC | GAG | GTC | TCC | ACG | TAC | CCG | CCC | GGC | 2326 |
| Thr | Thr | Tyr | Gln | Ile | Glu | Leu | Gly | Glu | Val | Ser | Thr | Tyr | Pro | Pro | Gly | |
| | | | | 645 | | | | | 650 | | | | | 655 | | |
| TAC | AAG | GAG | AAC | GGC | GGC | ATC | TTC | TGC | CAC | AAC | AAC | CCC | TGG | GTG | ATC | 2374 |
| Tyr | Lys | Glu | Asn | Gly | Gly | Ile | Phe | Cys | His | Asn | Asn | Pro | Trp | Val | Ile | |
| | | | 660 | | | | | 665 | | | | | 670 | | | |
| ATC | GCC | GAG | ACG | GTC | GTG | GGG | CGC | GGT | GCG | CAG | GCG | TTC | GAC | TAC | TAC | 2422 |
| Ile | Ala | Glu | Thr | Val | Val | Gly | Arg | Gly | Ala | Gln | Ala | Phe | Asp | Tyr | Tyr | |
| | | 675 | | | | | 680 | | | | | 685 | | | | |
| AAG | CGG | ATC | ACC | CCC | GCG | TAC | CGC | GAG | GAC | ATC | TCC | GAC | ACG | CAC | AAG | 2470 |
| Lys | Arg | Ile | Thr | Pro | Ala | Tyr | Arg | Glu | Asp | Ile | Ser | Asp | Thr | His | Lys | |
| | 690 | | | | | 695 | | | | | 700 | | | | | |
| CTC | GAG | CCG | TAC | GTG | TAC | GCG | CAG | ATG | ATC | GCG | GGC | AAG | GAG | GCG | GTG | 2518 |
| Leu | Glu | Pro | Tyr | Val | Tyr | Ala | Gln | Met | Ile | Ala | Gly | Lys | Glu | Ala | Val | |
| 705 | | | | 710 | | | | | 715 | | | | | 720 | | |
| CGC | GCC | GGC | GAG | GCG | AAG | AAC | TCG | TGG | CTC | ACC | GGA | ACG | GCG | GCG | TGG | 2566 |
| Arg | Ala | Gly | Glu | Ala | Lys | Asn | Ser | Trp | Leu | Thr | Gly | Thr | Ala | Ala | Trp | |
| | | | | 725 | | | | | 730 | | | | | 735 | | |
| AAC | TTC | GTC | GCG | GTG | TCC | CAG | TAC | CTG | CTG | GGC | GTG | CGG | CCC | GAC | TAC | 2614 |
| Asn | Phe | Val | Ala | Val | Ser | Gln | Tyr | Leu | Leu | Gly | Val | Arg | Pro | Asp | Tyr | |
| | | | 740 | | | | | 745 | | | | | 750 | | | |
| GAC | GGC | CTC | GTG | GTC | GAC | CCG | CAG | ATC | GGT | CCG | GAC | GTC | CCC | TCG | TAC | 2662 |
| Asp | Gly | Leu | Val | Val | Asp | Pro | Gln | Ile | Gly | Pro | Asp | Val | Pro | Ser | Tyr | |
| | | 755 | | | | | 760 | | | | | 765 | | | | |
| ACG | GTC | ACC | CGC | GTG | GCC | CGC | GGC | GCG | ACG | TAC | GAG | ATC | ACG | GTG | ACC | 2710 |
| Thr | Val | Thr | Arg | Val | Ala | Arg | Gly | Ala | Thr | Tyr | Glu | Ile | Thr | Val | Thr | |
| | 770 | | | | | 775 | | | | | 780 | | | | | |
| AAC | TCG | GGC | GCC | CCG | GGC | GCG | CGT | GCG | TCG | CTC | ACG | GTC | GAC | GGC | GCG | 2758 |
| Asn | Ser | Gly | Ala | Pro | Gly | Ala | Arg | Ala | Ser | Leu | Thr | Val | Asp | Gly | Ala | |
| 785 | | | | | 790 | | | | | 795 | | | | | 800 | |
| CCC | GTC | GAC | GGC | CGC | ACG | GTC | CCC | TAC | GCC | CCG | GCC | GGC | TCG | ACC | GTC | 2806 |
| Pro | Val | Asp | Gly | Arg | Thr | Val | Pro | Tyr | Ala | Pro | Ala | Gly | Ser | Thr | Val | |
| | | | | 805 | | | | | 810 | | | | | 815 | | |
| CGC | GTC | GAG | GTG | ACC | GTC | TGACCCGCGG | GTCCGACGGC | TGACGTCATG | | | | | | | | 2854 |
| Arg | Val | Glu | Val | Thr | Val | | | | | | | | | | | |
| | | | 820 | | | | | | | | | | | | | |

| | | | | | |
|---|---|---|---|---|---|
| ACGATGGTCC | AGGAGATCGA | GACGCCCGCG | CCGGCGGCCC | CTGCCGGCGC | GGGGGTCGCG | 2914 |
| CCCGAGCGCG | TCGTGACGCT | GCGCTCCGGT | GCGTGGGAGC | TCGACGTGCT | CCCGCGCACC | 2974 |
| GGGGCGGCCC | TCGGCGGTGG | CCGCATCCGC | ACCTCGGACG | GCGTGTGGCG | CGACCTGCTG | 3034 |
| CGCCCGACGC | GCCCGACCGT | CCTGGGCGAC | CCGGAGAAGT | GCTCGTCGTT | CCCGATGGTG | 3094 |
| CCGTGGTCCA | ACCGCATCCG | CGACGGCGTG | CTCGCCTTCG | GCGGGCGCTC | GTGGCAGCTG | 3154 |
| CAG | | | | | | 3157 |

( 2 ) INFORMATION FOR SEQ ID NO:2:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide (v) FRAGMENT TYPE: N-terminal (vi) ORIGINAL SOURCE:
    (A) ORGANISM: Cellvibrio gilvus
    (B) STRAIN: ATCC 13127
    (C) INDIVIDUAL ISOLATE: Direct Origin:

(vii) IMMEDIATE SOURCE:
    (B) CLONE: Digest of an enzyme produced by Cellvibrio gilvus (xi) SEQUENCE DESCRIPTION: SEQ ID NO:2:

```
Met  Arg  Tyr  Gly  His  Phe  Asp  Asp  Ala  Ala  Arg  Glu  Tyr  Val  Ile  Thr
1                   5                        10                       15

Thr  Pro  His  Thr  Pro  Tyr  Pro  Trp  Ile  Asn  Tyr  Leu  Gly  Ser  Glu  Gln
                    20                  25                       30

Phe  Phe  Ser  Leu  Leu  Ser  His  Gln
               35                  40
```

(2) INFORMATION FOR SEQ ID NO:3:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Cellvibrio gilvus
        (B) STRAIN: ATCC 13127
        (C) INDIVIDUAL ISOLATE: Direct Origin:

(vii) IMMEDIATE SOURCE:
        (B) CLONE: Digest of an enzyme produced by Cellvibrio gilvus (xi) SEQUENCE DESCRIPTION: SEQ ID NO:3:

```
Ala  Asp  Leu  Asp  His  Phe  Glu  Ala  Arg  His  Gly  Leu  Gly  Tyr  Ser  Arg
1                   5                        10                       15

Ile  Thr  Gly  Glu  Arg  Asn  Gly  Leu  Lys
                    20                  25
```

(2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Cellvibrio gilvus
        (B) STRAIN: ATCC 13127
        (C) INDIVIDUAL ISOLATE: Direct Origin:

(vii) IMMEDIATE SOURCE:
        (B) CLONE: Digest of an enzyme produced by Cellvibrio gilvus (xi) SEQUENCE DESCRIPTION: SEQ ID NO:4:

```
Val  Glu  Thr  Leu  Phe  Phe  Val  Pro  Leu  Gly  Glu  Asn  Ala  Glu  Val  Gln
1                   5                        10                       15

Lys
```

( 2 ) INFORMATION FOR SEQ ID NO:5:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Cellvibrio gilvus
        ( B ) STRAIN: ATCC 13127
        ( C ) INDIVIDUAL ISOLATE: Direct Origin:

( v i i ) IMMEDIATE SOURCE:
        ( B ) CLONE: Digest of an enzyme produced by Cellvibrio
            gilvus ( x i ) SEQUENCE DESCRIPTION: SEQ ID NO:5:

Val Thr Val Thr Asn Thr Ser Asp Ala Pro Lys
    1                5                        10

( 2 ) INFORMATION FOR SEQ ID NO:6:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Cellvibrio gilvus
        ( B ) STRAIN: ATCC 13127
        ( C ) INDIVIDUAL ISOLATE: Direct Origin:

( v i i ) IMMEDIATE SOURCE:
        ( B ) CLONE: Digest of an enzyme produced by Cellvibrio
            gilvus ( x i ) SEQUENCE DESCRIPTION: SEQ ID NO:6:

Thr Glu Tyr Arg Glu Arg Arg Asp His Tyr Ala Val Phe Gly Val Asn
    1                5                      10                      15

Thr Arg Ala Asp Gly Phe Asp Thr Asp Arg Asp Thr Phe Val Gly
                  20                      25                    30

( 2 ) INFORMATION FOR SEQ ID NO:7:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Cellvibrio gilvus
        ( B ) STRAIN: ATCC 13127
        ( C ) INDIVIDUAL ISOLATE: Direct Origin:

( v i i ) IMMEDIATE SOURCE:
        ( B ) CLONE: Digest of an enzyme produced by Cellvibrio
            gilvus ( x i ) SEQUENCE DESCRIPTION: SEQ ID NO:7:

Ser Ala Asp Ser Val Ala Ser Gly Trp Tyr Pro Ile Gly Ser His Ser
1               5                   10                  15

Val Ala ( 2 ) INFORMATION FOR SEQ ID NO:8:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Cellvibrio gilvus
        ( B ) STRAIN: ATCC 13127
        ( C ) INDIVIDUAL ISOLATE: Direct Origin:

( v i i ) IMMEDIATE SOURCE:
        ( B ) CLONE: Digest of an enzyme produced by Cellvibrio
            gilvus ( x i ) SEQUENCE DESCRIPTION: SEQ ID NO:8:

Trp Ala Asp Asp Ala His Gln Val Val Asn Lys
1               5                   10

( 2 ) INFORMATION FOR SEQ ID NO:9:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Cellvibrio gilvus
        ( B ) STRAIN: ATCC 13127
        ( C ) INDIVIDUAL ISOLATE: Direct Origin:

( v i i ) IMMEDIATE SOURCE:
        ( B ) CLONE: Digest of an enzyme produced by Cellvibrio
            gilvus ( x i ) SEQUENCE DESCRIPTION: SEQ ID NO:9:

Ala Pro Ala His Ala Leu Leu Gly Arg Phe Ala Thr Ser Glu Gln Val
1               5                   10                  15

Asp Ala Ala Leu Glu Ala Leu Asn Ser Tyr Trp Thr Asn Leu Leu
                20                  25                  30

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Cellvibrio gilvus
        ( B ) STRAIN: ATCC 13127

(C) INDIVIDUAL ISOLATE: Direct Origin:

(vii) IMMEDIATE SOURCE:
    (B) CLONE: Digest of an enzyme produced by Cellvibrio gilvus (xi) SEQUENCE DESCRIPTION: SEQ ID NO:10:

```
Arg Gly Asn Asn Asp Ile Gly Ser Gly Phe Asn Asp Asp Pro
1               5                   10
```

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Cellvibrio gilvus
        (B) STRAIN: ATCC 13127
        (C) INDIVIDUAL ISOLATE: Direct Origin:

(vii) IMMEDIATE SOURCE:
        (B) CLONE: Digest of an enzyme produced by Cellvibrio gilvus (xi) SEQUENCE DESCRIPTION: SEQ ID NO:11:

```
Tyr Val Asp Glu Val Arg Ala
1               5
```

(2) INFORMATION FOR SEQ ID NO:12:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Cellvibrio gilvus
        (B) STRAIN: ATCC 13127
        (C) INDIVIDUAL ISOLATE: Direct Origin:

(vii) IMMEDIATE SOURCE:
        (B) CLONE: Digest of an enzyme produced by Cellvibrio gilvus (xi) SEQUENCE DESCRIPTION: SEQ ID NO:12:

```
Ile Trp Ile Glu Pro Gln Gly Phe Ala Val Met Ala Gly Ile Gly Val
1               5                   10                  15
Gly Glu Gly Pro Asp Asp Ala Asp Ala Pro Ala Val Lys
                20                  25
```

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PREPARED FROM AMINO ACID SEQUENCE"

(v i) ORIGINAL SOURCE:
  (A) ORGANISM: Cellvibrio gilvus
  (B) STRAIN: ATCC 13127
  (C) INDIVIDUAL ISOLATE: Direct Origin:

(v i i) IMMEDIATE SOURCE:
  (B) CLONE: Digest of an enzyme produced by Cellvibrio gilvus (x i) SEQUENCE DESCRIPTION: SEQ ID NO:13:

GARTAYGTSA TYACSAC                                                                              17

(2) INFORMATION FOR SEQ ID NO:14:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "PREPARED FROM AMINO ACID SEQUENCE"

(v i) ORIGINAL SOURCE:
    (A) ORGANISM: Cellvibrio gilvus
    (B) STRAIN: ATCC 13127
    (C) INDIVIDUAL ISOLATE: Direct Origin:

(v i i) IMMEDIATE SOURCE:
    (B) CLONE: Digest of an enzyme produced by Cellvibrio gilvus (x i) SEQUENCE DESCRIPTION: SEQ ID NO:14:

ACCTGRTGBG CRTCRTC                                                                              17

(2) INFORMATION FOR SEQ ID NO:15:

(i) SEQUENCE CHARACTERISTICS:
    (A) LENGTH: 821 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "PCR PRODUCT"

(v i) ORIGINAL SOURCE:
    (A) ORGANISM: Cellvibrio gilvus
    (B) STRAIN: ATCC 13127

(x i) SEQUENCE DESCRIPTION: SEQ ID NO:15:

GAGTACGTCA TCACGACGCC TCACACCCCC TACCCGTGGA TCAACTACCT CGGGTCGGAG    60

CAGTTCTTCT CGCTGCTCTC CCACCAGGCC GGCGGCTACT CGTTCTACCG CGACGCCAAG   120

ATGCGGCGGC TCACGCGCTA CCGCTACAAC AACATCCCCG CGGACGCGGG CGGCCGGTAC   180

CTGTACGTCA ACGACGGCGG CGACGTGTGG ACCCCGTCGT GGCTGCCGGT CAAGGCGGAC   240

CTGGACCACT TCGAGGCGCG CCACGGCCTC GGCTACTCGC GCATCACGGG CGAGCGCAAC   300

GGCCTGAAGG TCGAGACGCT CTTCTTCGTC CCGCTCGGCG AGAACGCCGA GGTGCAGAAG   360

GTCACCGTCA CCAACACGTC CGACGCCCCG AAGACGGCGA CGCTGTTCTC GTTCGTCGAG   420

TTCTGCCTGT GGAACGCGCA GGACGACCAG ACGAACTACC AGCGCAACCT GTCGATCGGC   480

GAGGTCGAGG TCGAGCAGGA CGGCCCGCAC GGCTCGGCGA TCTACCACAA GACCGAGTAC   540

CGCGAGCGCC GCGACCACTA CGCCGTGTTC GGCGTGAACA CCCGCGCGGA CGGCTTCGAC   600

ACGGACCGCG ACACGTTCGT GGGCGCGTAC AACTCGCTGG GCGAGGCGTC CGTCCCGCGC   660

```
GCCGGGAAGT  CCGCGGACTC  GGTCGCGTCG  GGCTGGTACC  CGATCGGCTC  GCACTCCGTC        720

GCCGTGACGC  TGCAGCCCGG  CGAGTCCCGC  GACCTCGTCT  ACGTGCTGGG  CTACCTGGAG        780

AACCCCGACG  AGGAGAAGTG  GGCCGACGAC  GCCCACCAGG  T                            821
```

( 2 ) INFORMATION FOR SEQ ID NO:16:

( i ) SEQUENCE CHARACTERISTICS:
        ( A ) LENGTH: 822 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met  Arg  Tyr  Gly  His  Phe  Asp  Asp  Ala  Ala  Arg  Glu  Tyr  Val  Ile  Thr
 1              5                    10                       15

Thr  Pro  His  Thr  Pro  Tyr  Pro  Trp  Ile  Asn  Tyr  Leu  Gly  Ser  Glu  Gln
              20                   25                        30

Phe  Phe  Ser  Leu  Leu  Ser  His  Gln  Ala  Gly  Gly  Tyr  Ser  Phe  Tyr  Arg
         35                        40                       45

Asp  Ala  Lys  Met  Arg  Arg  Leu  Thr  Arg  Tyr  Arg  Tyr  Asn  Asn  Ile  Pro
    50                        55                        60

Ala  Asp  Ala  Gly  Gly  Arg  Tyr  Leu  Tyr  Val  Asn  Asp  Gly  Gly  Asp  Val
65                       70                        75                         80

Trp  Thr  Pro  Ser  Trp  Leu  Pro  Val  Lys  Ala  Asp  Leu  Asp  His  Phe  Glu
                   85                        90                   95

Ala  Arg  His  Gly  Leu  Gly  Tyr  Ser  Arg  Ile  Thr  Gly  Glu  Arg  Asn  Gly
              100                       105                      110

Leu  Lys  Val  Glu  Thr  Leu  Phe  Phe  Val  Pro  Leu  Gly  Glu  Asn  Ala  Glu
         115                       120                      125

Val  Gln  Lys  Val  Thr  Val  Thr  Asn  Thr  Ser  Asp  Ala  Pro  Lys  Thr  Ala
    130                       135                      140

Thr  Leu  Phe  Ser  Phe  Val  Glu  Phe  Cys  Leu  Trp  Asn  Ala  Gln  Asp  Asp
145                       150                       155                       160

Gln  Thr  Asn  Tyr  Gln  Arg  Asn  Leu  Ser  Ile  Gly  Glu  Val  Glu  Val  Glu
                  165                       170                      175

Gln  Asp  Gly  Pro  His  Gly  Ser  Ala  Ile  Tyr  His  Lys  Thr  Glu  Tyr  Arg
              180                       185                      190

Glu  Arg  Arg  Asp  His  Tyr  Ala  Val  Phe  Gly  Val  Asn  Thr  Arg  Ala  Asp
         195                       200                      205

Gly  Phe  Asp  Thr  Asp  Arg  Asp  Thr  Phe  Val  Gly  Ala  Tyr  Asn  Ser  Leu
    210                       215                      220

Gly  Glu  Ala  Ser  Val  Pro  Arg  Ala  Gly  Lys  Ser  Ala  Asp  Ser  Val  Ala
225                       230                       235                       240

Ser  Gly  Trp  Tyr  Pro  Ile  Gly  Ser  His  Ser  Val  Ala  Val  Thr  Leu  Gln
                  245                       250                      255

Pro  Gly  Glu  Ser  Arg  Asp  Leu  Val  Tyr  Val  Leu  Gly  Tyr  Leu  Glu  Asn
              260                       265                      270

Pro  Asp  Glu  Glu  Lys  Trp  Ala  Asp  Ala  His  Gln  Val  Val  Asn  Lys
         275                       280                      285

Ala  Pro  Ala  His  Ala  Leu  Leu  Gly  Arg  Phe  Ala  Thr  Ser  Glu  Gln  Val
    290                       295                      300

Asp  Ala  Ala  Leu  Glu  Ala  Leu  Asn  Ser  Tyr  Trp  Thr  Asn  Leu  Leu  Ser
305                       310                       315                       320

Thr  Tyr  Ser  Val  Ser  Ser  Thr  Asp  Glu  Lys  Leu  Asp  Arg  Met  Val  Asn
                  325                       330                      335
```

```
Ile  Trp  Asn  Gln  Tyr  Gln  Cys  Met  Val  Thr  Phe  Asn  Met  Ser  Arg  Ser
               340                 345                          350

Ala  Ser  Phe  Phe  Glu  Thr  Gly  Ile  Gly  Arg  Gly  Met  Gly  Phe  Arg  Asp
               355                 360                          365

Ser  Asn  Gln  Asp  Leu  Leu  Gly  Phe  Val  His  Leu  Ile  Pro  Glu  Arg  Ala
               370                 375                          380

Arg  Glu  Arg  Ile  Ile  Asp  Ile  Ala  Ser  Thr  Gln  Phe  Ala  Asp  Gly  Ser
385                           390                 395                          400

Ala  Tyr  His  Gln  Tyr  Gln  Pro  Leu  Thr  Lys  Arg  Gly  Asn  Asn  Asp  Ile
               405                 410                          415

Gly  Ser  Gly  Phe  Asn  Asp  Asp  Pro  Leu  Trp  Leu  Ile  Ala  Gly  Val  Ala
               420                 425                          430

Ala  Tyr  Ile  Lys  Glu  Ser  Gly  Asp  Trp  Gly  Ile  Leu  Asp  Glu  Pro  Val
               435                 440                          445

Pro  Phe  Asp  Asn  Glu  Pro  Gly  Ser  Glu  Val  Pro  Leu  Phe  Glu  His  Leu
               450                 455                          460

Thr  Arg  Ser  Phe  Gln  Phe  Thr  Val  Gln  Asn  Arg  Gly  Pro  His  Gly  Leu
465                           470                 475                          480

Pro  Leu  Ile  Gly  Arg  Ala  Asp  Trp  Asn  Asp  Cys  Leu  Asn  Leu  Asn  Cys
               485                 490                          495

Phe  Ser  Thr  Thr  Pro  Gly  Glu  Ser  Phe  Gln  Thr  Thr  Glu  Asn  Gln  Ala
               500                 505                          510

Gly  Gly  Val  Ala  Glu  Ser  Val  Phe  Ile  Ala  Ala  Gln  Phe  Val  Leu  Tyr
               515                 520                          525

Gly  Ala  Glu  Tyr  Ala  Thr  Leu  Ala  Glu  Arg  Arg  Gly  Leu  Ala  Asp  Val
               530                 535                          540

Ala  Thr  Glu  Ala  Arg  Lys  Tyr  Val  Asp  Glu  Val  Arg  Ala  Ala  Val  Leu
545                           550                 555                          560

Glu  His  Gly  Trp  Asp  Gly  Gln  Trp  Phe  Leu  Arg  Ala  Tyr  Asp  Tyr  Tyr
               565                 570                          575

Gly  Asn  Pro  Val  Gly  Thr  Asp  Ala  Lys  Pro  Glu  Gly  Lys  Ile  Trp  Ile
               580                 585                          590

Glu  Pro  Gln  Gly  Phe  Ala  Val  Met  Ala  Gly  Ile  Gly  Val  Gly  Glu  Gly
               595                 600                          605

Pro  Asp  Ala  Asp  Ala  Pro  Ala  Val  Lys  Ala  Leu  Asp  Ser  Val  Asn
               610                 615                          620

Glu  Met  Leu  Gly  Thr  Pro  His  Gly  Leu  Val  Leu  Gln  Tyr  Pro  Ala  Tyr
625                           630                 635                          640

Thr  Thr  Tyr  Gln  Ile  Glu  Leu  Gly  Glu  Val  Ser  Thr  Tyr  Pro  Pro  Gly
               645                 650                          655

Tyr  Lys  Glu  Asn  Gly  Gly  Ile  Phe  Cys  His  Asn  Asn  Pro  Trp  Val  Ile
               660                 665                          670

Ile  Ala  Glu  Thr  Val  Val  Gly  Arg  Gly  Ala  Gln  Ala  Phe  Asp  Tyr  Tyr
               675                 680                          685

Lys  Arg  Ile  Thr  Pro  Ala  Tyr  Arg  Glu  Asp  Ile  Ser  Asp  Thr  His  Lys
690                           695                 700

Leu  Glu  Pro  Tyr  Val  Tyr  Ala  Gln  Met  Ile  Ala  Gly  Lys  Glu  Ala  Val
705                           710                 715                          720

Arg  Ala  Gly  Glu  Ala  Lys  Asn  Ser  Trp  Leu  Thr  Gly  Thr  Ala  Ala  Trp
               725                 730                          735

Asn  Phe  Val  Ala  Val  Ser  Gln  Tyr  Leu  Leu  Gly  Val  Arg  Pro  Asp  Tyr
               740                 745                          750

Asp  Gly  Leu  Val  Val  Asp  Pro  Gln  Ile  Gly  Pro  Asp  Val  Pro  Ser  Tyr
```

-continued

|  | | | | | 755 | | | | | 760 | | | | | 765 | | |
|---|---|---|---|---|---|---|---|---|---|---|---|---|---|---|---|---|---|
| Thr | Val | Thr | Arg | Val | Ala | Arg | Gly | Ala | Thr | Tyr | Glu | Ile | Thr | Val | Thr | | |
| | 770 | | | | | 775 | | | | | 780 | | | | | | |
| Asn | Ser | Gly | Ala | Pro | Gly | Ala | Arg | Ala | Ser | Leu | Thr | Val | Asp | Gly | Ala | | |
| 785 | | | | | 790 | | | | | 795 | | | | | 800 | | |
| Pro | Val | Asp | Gly | Arg | Thr | Val | Pro | Tyr | Ala | Pro | Ala | Gly | Ser | Thr | Val | | |
| | | | | 805 | | | | | 810 | | | | | 815 | | | |
| Arg | Val | Glu | Val | Thr | Val | | | | | | | | | | | | |
| | | | 820 | | | | | | | | | | | | | | |